United States Patent [19]

Hennessy

[11] 4,078,313

[45] Mar. 14, 1978

[54] MEASURING DEVICE

[76] Inventor: John Brian Hennessy, Ahuroa, North Auckland, New Zealand

[21] Appl. No.: 746,638

[22] Filed: Dec. 1, 1976

[30] Foreign Application Priority Data

Jan. 12, 1975 New Zealand .......... 179410

[51] Int. Cl.² ............ G01B 3/22; G01B 5/02
[52] U.S. Cl. ................................. 33/169 B
[58] Field of Search ............ 33/169 R, 169 B, 172 R, 33/172 E

[56] References Cited

U.S. PATENT DOCUMENTS

| 2,053,938 | 9/1936 | Barker | 33/126.7 A |
| 2,127,042 | 8/1938 | Morrell | 33/126.7 A |
| 2,763,935 | 9/1956 | Whaley et al. | 33/169 B |
| 3,478,435 | 11/1969 | Cook | 33/169 B |

Primary Examiner—Harry N. Haroian
Attorney, Agent, or Firm—Wenderoth, Lind & Ponack

[57] ABSTRACT

A measuring device includes a probe having a light source and a light sensitive diode therein such that light reflected from the surroundings of the probe can be detected by the light sensitive diode. A reference is provided such that the depth of the probe in, for example, animal fat can be measured and in particular the point at which the probe passes from fat to lean meat can be determined. A suitable scale or other indicating device is provided.

6 Claims, 7 Drawing Figures

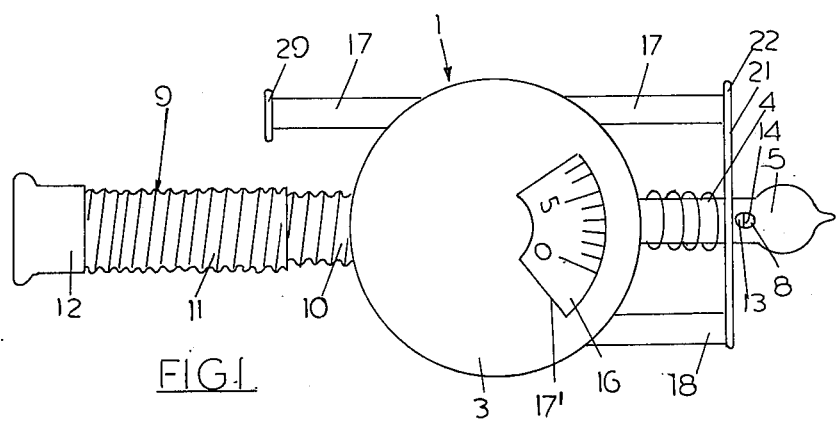
FIG.1.
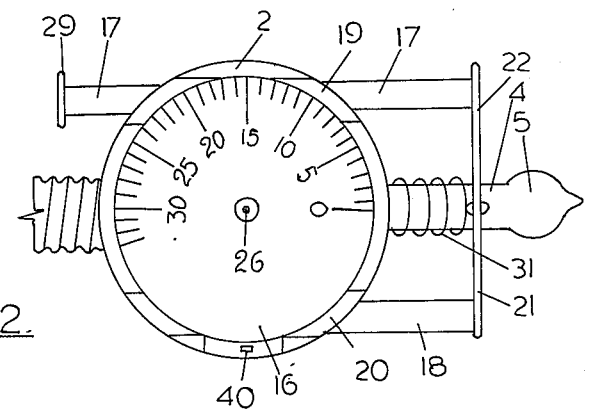
FIG.2.
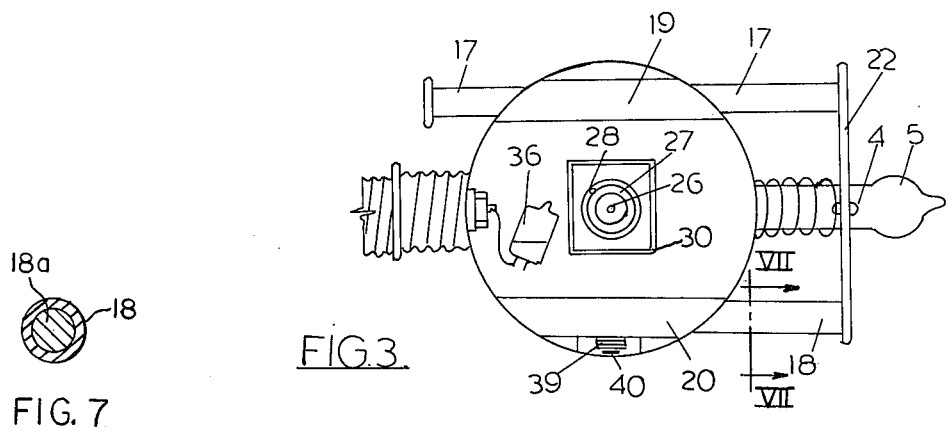
FIG.3.
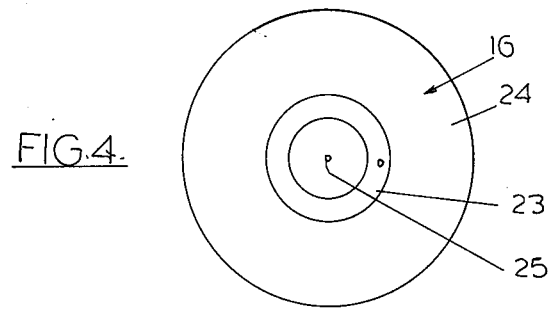
FIG. 7
FIG.4.

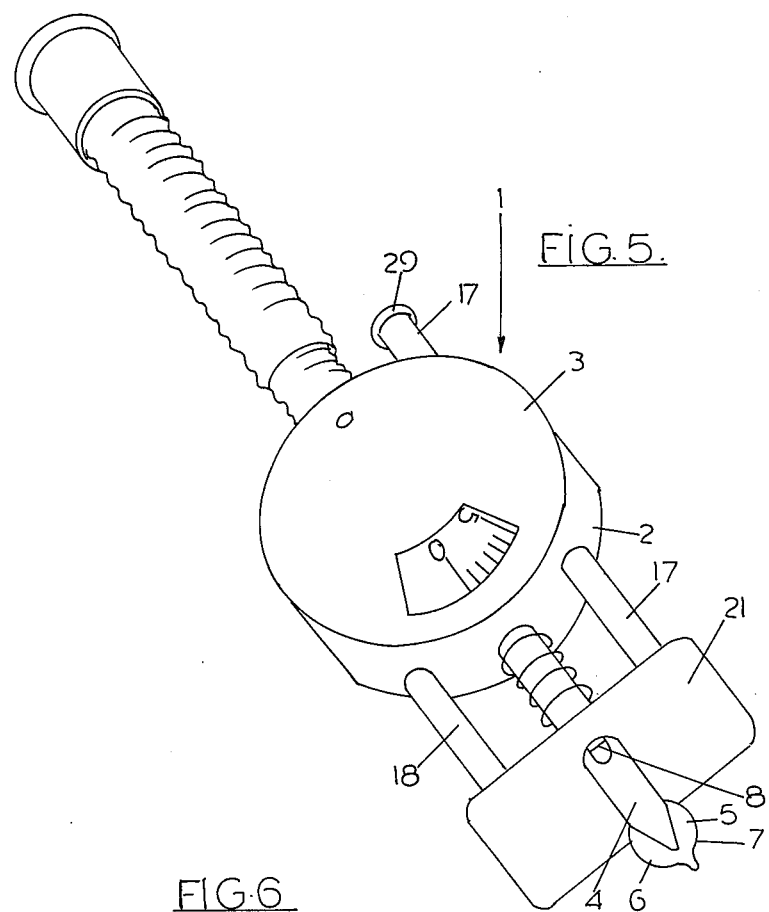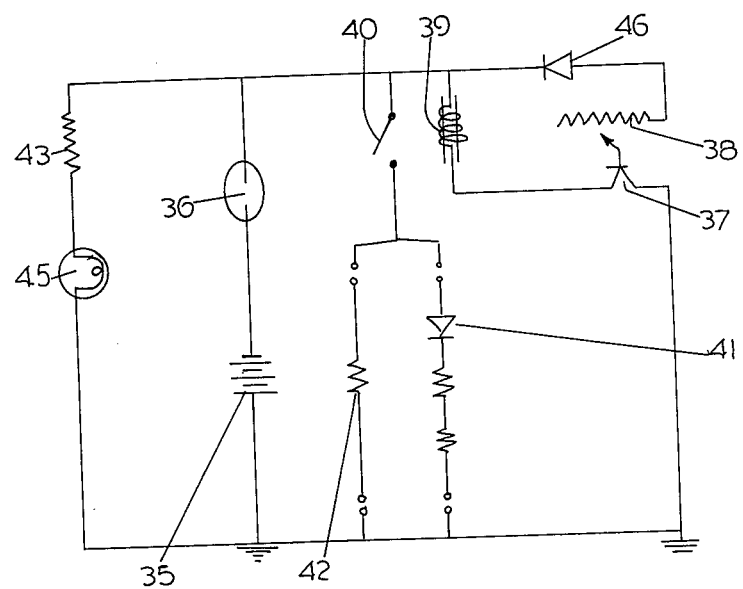

MEASURING DEVICE

BACKGROUND OF THE INVENTION

This invention relates to a measuring device.

In the meat industry it is frequently desirable or even necessary to know the thickness of fat on an animal so that the animal can be graded according to quality. Hitherto this has been an extremely difficult operation to perform as it has been necessary to make an incision into the fat, insert a measuring device therein and view a scale through the device. This difficulty has been compounded as the scale has been poorly lit and therefore difficult to read and also in many instances the operation must be performed while the carcass is moving thus leading to a tendency to conduct the taking of the measurement in an unsatisfactory or incomplete manner.

SUMMARY OF THE INVENTION

It is therefore an object of the present invention to provide a measuring device which will go some way towards obviating or minimising the foregoing disadvantages in a simple yet effective manner or which will at least provide the public with a useful choice.

Accordingly, the invention consists of a measuring device comprising a probe having an aperture in the wall thereof, sensing means within the probe and including a light source and a light sensitive element adjacent the aperture arranged such that the light source emits light which if reflected by the surrounding environment is sensed by the light sensitive element, distance measuring means to measure the distance between a reference point and the position where the light sensitive element begins or ceases to sense light, and indicator means to indicate whether or not light is being sensed by the light sensitive element.

To those skilled in the art to which this invention relates, many changes in construction and widely differing embodiments and applications of the invention will suggest themselves without departing from the scope of the invention as defined in the appended claims. The disclosures and the description herein are purely illustrative and are not intended to be in any sense limiting.

BRIEF DESCRIPTION OF THE DRAWINGS

One preferred form of the invention and modification thereof will now be described with reference to the accompanying drawings in which FIG. 1 is a plan view of a measuring device according to the invention, FIG. 2 is a plan view of part of a measuring device according to the invention the cover being shown as removed.

FIG. 3 is a plan view of part of a measuring device according to the invention the scale being shown as removed and, for the purposes of clarity, the wiring not being shown.

FIG. 4 is an underneath view of the scale,

FIG. 5 is a perspective view of a measuring device according to the invention,

FIG. 6 is a circuit diagram of one form of wiring available for use according to the invention although other circuits could be used; and FIG. 7 is a cross-section taken along line VII—VII in FIG. 3.

DETAILED DESCRIPTION OF THE INVENTION

In the preferred form of the invention a distance measuring device 1 is provided as follows:

The distance measuring device comprises a body 2 in the form of a hollow member being closable by a lid or cover 3. From the body 2 extends a probe 4 the leading edge of which may include a spear or other sharpened point 5. For example, the edges 6 and 7 may be sharpened such that the spear 5 is capable of making an incision for example, through the fatty layer in particular of an animal such as a pig, cow, sheep or any other animal. The probe 4 is preferably hollow, at least from the body 2 to a reference point indicated generally at 8 in FIGS. 1 and 5 as will be described later. The lid 3 is preferably able to be sealed to the hollow body part 2 and for example, a suitable sealant may be spread or otherwise positioned between the lid 3 and the body part 2 during the manufacturing process. A handle 9 extends from the body which handle 9 is preferably hollow and may comprise three parts—10, 11 and 12, the part 10 including parts of the electric and/or electronic circuitry, the part 11 comprising a housing for the provision of batteries and the part 12 comprising a closure cap, the contacts for the batteries being provided, for example, in the parts 10 and 12 in, for example, substantially the manner known for torches.

In an alternative construction it is envisaged that the handle could be provided basically for gripping purposes and the power supply could be provided by mains supply fed through suitable transformers to reduce the voltage to the desired level such as 6 to 12 volts.

In one form of the invention an aperture 13 is provided in the probe 4 and optic fibres are led through from the body 2 to the aperture 13, one optic fibre leading from, for example, a light source operated by the battery or other power supply and the other optic fibre leading, for example, to a photo cell forming part of an electrical circuit. A dividing plate indicated at 14 may be provided between the outlets of the two optic fibres.

In an alternative and preferred construction a lamp 45, see FIG. 6, may be provided on one side of the plate 14 and on the other side of the plate 14 may be provided a photo sensitive diode 46 again forming part of an electronic or electric circuit as will be described later. In this construction suitable wires are led from the body 2 to the lamp and photo sensitive diode rather than optic fibres.

Indicator means are provided which may comprise for example, a tactile stimulator or a light source which is switched on or off when the change of condition or surroundings occurs and for example, is preferably switched on. Again the light or stimulator may be operated from the battery circuit or other circuit above mentioned. In the preferred form however, the indicator means comprises a scale 16 marked for example in milimeters, or in any other suitable distance measuring dimension, and the scale may be viewed through an aperture 17' through the lid 3 which aperture 17 may be opened, but is preferably closed for example, by glass or perspex or other transparent material. A reference marking may be provided for example, on the transparent plate but the reference marking is not shown in the drawings.

Distance measuring means are provided and these may comprise a rod or shaft or rods or shafts 17 and 18 passing through apertures in the body 2 and they may pass through hollow, for example, tubular members 19 and 20 passing through the hollow member. Thus, the hollow members 19 and 20 may be in the form of sealed tubes passing through the hollow body 2. The rods 17 and 18 are moveable through the tubes 19 and 20. The ends of one or both rods 17 and 18 provide a further reference point and it is the distance between this reference point and the reference point 14 which is to be measured. The size of the ends of the rods 17 and 18 may by increased by providing a plate 21 the front face 22 of which is to provide in fact a reference point. The movement of the reference point at face 22 may be caused to effect the scale by providing for example, a bar magnet 18a within one of the rods 17 or 18, for example, the rod 18, and by providing a circular or annular magnet 23 polarised for example, by north and south poles as indicated at FIG. 4. The arrangement may also have a multiplicity of north and south poles arranged around the circumference of the annular magnets 23. The scale 16 may be formed from a sheet of non-magnetic material 18 on which the scale markings are marked. The magnet 23 is adhered preferably to the under side of the plate 24 and an aperture 25 is provided through the plate 24 and a pin 26 is affixed in the body 2 about which the scale 16 rotates. Thus the pin 26 may be affixed for example, to a bearing 27 which is affixed to the base of the body 2 and through which a screw 28 passes able to tighten onto the pin 26.

In an alternative construction movements of the bar magnet may be caused to effect another device such as a field effect transistor such that a varying current flow can be caused by movement of the bar magnet which varying current flow could be measured and used to operate a printer or the like such that a print-out perhaps in the form of a ticket could be provided which can be engaged with the article being measured.

An abutment 29 may be provided on the rod 17 such that some control of the rod 17 can be gained from the hand, for example, the thumb of the user.

Also an enclosure 30 may be provided within the body 2 constructed from for example aluminium, such that the movement of the circular magnet within the box 30 will give rise to eddy currents within the box 30, the eddy currents acting as a break so as to substantially prevent too rapid and too extreme swinging of the scale 16.

Also a spring 31 may be provided between the body 2 and the plate 21 so as to return the plate 21 to substantially a rest position after use and also to provide a resistance against which the plate 21 must be pushed in use.

In the circuit shown in FIG. 6 the lamp 45 and light sensitive diode 46 are provided within the probe as above described and where necessary a filter may be provided over for example, the photo-sensitive diode such as to eliminate undesirable reflections and thus for example, a yellow filter may be provided where for example, fat depth is to be measured and the fat has a yellow colour. This gives the fat and meat an overall yellowness as seen by the diode and allows spurious readings to be substantially eliminated.

In the circuit a power supply 35 is provided which may be a battery as shown or a mains supply as above mentioned and a mercury switch 36 may be provided which acts, for example, as a battery saving device such that when the construction is lain down the terminals of the mercury switch 36 will not be covered by the mercury and the device is therefore switched off.

A switching transistor 37 is provided and a rheostat 38 which can be adjusted, for example, by operating a screw and the rheostat 38 may be provided in the part 10 of the handle. A closure with an aperture therein may be provided such that the rheostat may be adjusted by passing a screw driver partly through the aperture and adjusting a screw thus varying the resistance of the rheostat 38.

A brake or clamp is preferably provided to clamp the scale in the position where the change of condition or surrounding occurs and the clamp may, for example, include a relay 39 operating a reed 40 which reed 40 may clamp against the perimeter of the scale 16. If desired, a light emitting diode or other lamp 41 may be included in the circuit which again provides an indication of the depth that the change of condition or surrounding occurs and this is shown as an alternative in FIG. 6. If the lamp 41 is not provided a resistor 42 is preferably provided in the circuit shown in FIG. 6 and in the preferred use of the invention the clamp will operate as the reference point 14 passes from, for example, fat to meat in a carcass, but by re-arranging the circuit the clamping can be caused to occur as the scale is withdrawn from meat to fat and this can be achieved by re-arranging the switching circuit including the transistor 37 for example, by including a further switching transistor, in substantially the known manner. The resistor 43 may also comprise a rheostat to enable the sensitivity of the arrangement to be varied and this rheostat may be adjusted in substantially the same manner as the rheostat 38.

Although a particular construction has been described above it will be clear that many modifications to the construction are possible where a distance is to be measured between a reference point and a point where a change in condition or surroundings take place and merely by way of further example the apparatus could be used as a depth measuring device where the probe is lowered such that when a certain light intensity is reached the change of condition occurs and for example, an indication is obtained but other uses of the invention are envisaged.

The use of the invention in the preferred form is as follows:

The probe 4 is inserted, for example into the carcass of an animal, for example a pig carcass or in constructions where suitable colour filters are used into the carcass for example of cattle or sheep and whilst the aperture 13 with the reference point 14 therein is passing through fat light reflections will occur and the photo sensitive diode will in the construction shown in FIG. 6 operate in such a way that the transistor 37 is switched off. When the reference point passes from fat to lean meat for example in the muscle of an animal, sufficient light to operate the diode 46 will no longer be reflected back to the diodes 46 and the transistor 37 will switch on thus causing the solenoid 39 to draw in the relay 40 which thereby clamps on the perimeter of the scale 16 thus fixing the scale 16 at a reading showing the depth of fat on the carcass. Alternatively the fixing can be caused to occur as the probe is withdrawn. The scale will of course have been caused to revolve by virtue of the other reference point, i.e. the face 22 bearing on the outside of the carcass and as the probe 4 is inserted the spring 31 is compressed and the bar magnet is moved through the sealed hollow member 19 or the sealed hollow member 20 thus causing the magnet 23 to rotate thus rotating the scale.

In the other constructions suitable print-outs showing the depth or other indications are given.

As the spike is withdrawn the spring 31 will return the construction to substantially an equilibrium position.

Thus it can be seen that a distance measuring device is provided which will allow distances to be measured in a simple yet effective manner without the necessity of making original incisions in a carcass and this is desirable.

Also the scale is easily read even when the carcass is moving and the construction is simple to operate and can be made conformable by providing a desirable angle between the handle and spike.

It is a particular advantage of the invention that the construction can be made such that there are no unsealed entry into the body and thus the whole apparatus can be completely sterilised without damage to the internal parts, and also tampering with the device is made relatively difficult.

I claim:

1. A measuring device comprising:
   a probe having an aperture in a wall thereof;
   sensing means positioned within said probe and including a light source and a light sensitive element positioned adjacent said aperture such that said light source emits light outwardly through said aperture, which light if reflected by the surrounding environment passes inwardly through said aperture and is sensed by said light sensitive element;
   distance measuring means, operatively connected to said probe and said sensing means, for measuring the distance of movement of said probe between a reference first point and a second point whereat said light sensitive element begins or ceases to sense reflected light, as a function of the light reflecting nature of the environment surrounding said aperture; and
   indicator means operable by said distance measuring means for indicating whether said light sensitive element is sensing reflected light.

2. A measuring device as claimed in claim 1, further comprising a body, and said probe comprising a hollow spike extending from said body.

3. A measuring device as claimed in claim 2, wherein said distance measuring means comprises an aperture through said body, and a shaft movably passing through said aperture and aligned to be substantially parallel to said spike.

4. A measuring device as claimed in claim 3, wherein said distance measuring means further includes a scale.

5. A measuring device as claimed in claim 4, wherein said shaft includes a bar magnet, and said scale is mounted on a rotatable magnet so that movement of said shaft causes said bar magnet to effect the rotatable magnet to move said scale.

6. A measuring device as claimed in claim 5, wherein said indicator means comprises a clamp arranged to clamp said scale into the position it holds when said light sensitive element begins or ceases to sense reflected light.

* * * * *